United States Patent

Messer, Jr. et al.

Patent Number: 5,726,179
Date of Patent: Mar. 10, 1998

[54] MUSCARINIC AGONISTS

[75] Inventors: William S. Messer, Jr., Toledo, Ohio; Babatunde Ojo, Richmond, Va.

[73] Assignee: The University of Toledo, Toledo, Ohio

[21] Appl. No.: 625,144

[22] Filed: Apr. 1, 1996

[51] Int. Cl.$^6$ ................ C07D 403/04; A61K 31/505
[52] U.S. Cl. ........................... 514/256; 544/333
[58] Field of Search ...................... 544/333; 514/256

[56] References Cited

U.S. PATENT DOCUMENTS 5,175,166  12/1992  Dunbar et al. .
5,403,845   4/1995  Dunbar et al. .

*Primary Examiner*—Patricia L. Morris
*Attorney, Agent, or Firm*—Brinks Hofer Gilson & Lione

[57] ABSTRACT

A muscarinic agonist compound having the formula (I) or (II) below or a pharmaceutically acceptable salt thereof:

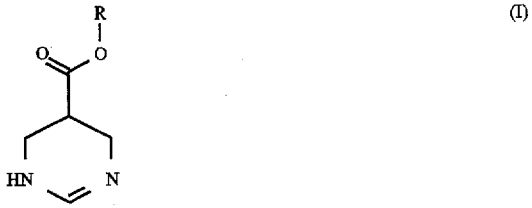

(I)

where R is (trans) 3-methyl-2-penten-4-ynyl, (cis)3-methyl-2-penten-4-ynyl, 2-butynyl, 2-methylbutenyl, 3-methylpropynyl, phenylpropynyl, butynyl; or

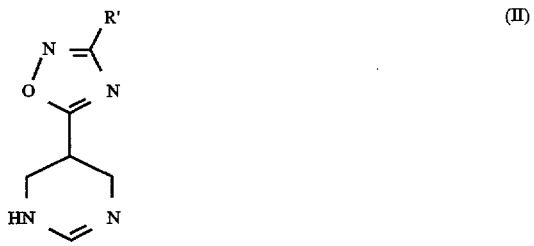
(II)

where R' is butynyl.

3 Claims, No Drawings

MUSCARINIC AGONISTS

The present invention relates to amidine derivative compounds having binding affinities and/or agonist activity at muscarinic receptors in the central nervous system.

BACKGROUND OF THE INVENTION

The University of Toledo U.S. Pat. Nos. 5,175,166 and 5,403,845 (Dunbar, Durant, Hoss and Messer) disclose muscarinic agonists and are hereby incorporated by reference. As stated therein, there is a need in the art to provide muscarinic agonists which have activity various muscarinic receptors subtypes in the central nervous system.

The neurotransmitter acetylcholine mediates a variety of responses within the central nervous system and plays an important role in memory function and cognition. Cholinergic responses are mediated by muscarinic and nicotinic receptors throughout the brain, although it is accepted generally that receptors in the cerebral cortex and hippocampus are associated with memory and cognitive function. Agents that block acetylcholine activity at muscarinic receptors and lesions of Cholinergic projections to the cortex and hippocampus impair memory and cognition.

In humans, the nucleus basalis of Meynert is the source of acetylcholine for the cerebral cortex and hippocampus. The cholinergic cells within the basal nucleus degenerate in Alzheimer's disease, a disorder that is associated with memory dysfunction and progressive cognitive decline. Current therapeutic approaches for Alzheimer's disease include treatment with agents that increase levels of acetylcholine or mimic the effects of acetylcholine at receptors.

Efforts to increase acetylcholine levels have focused on increasing levels of choline, the precursor for acetylcholine synthesis, and on blocking acetylcholinesterase (AChEase), the enzyme that metabolizes acetylcholine. The first approach, using either choline or phosphatidylcholine, has not been very successful although acetylcholinesterase inhibitors have shown some therapeutic efficacy. Clinical trials with these compounds have documented some improvements in cognitive function and ability to conduct daily tasks. Major drawbacks with AChEase inhibitors include toxicity and the side effects associated with activation of receptors in the peripheral nervous system.

Recent efforts have focused on treating Alzheimer's patients with agonists for muscarinic cholinergic receptors. Natural products, such as the arecoline and pilocarpine ligands, can mimic the effects of acetylcholine at receptors in the central nervous system and reverse cognitive impairments in experimental animals. The clinical application of such ligands is hampered however by the low intrinsic activity of these compounds and their rapid metabolism. Other muscarinic agonists with higher efficacy are not suitable due to either low bioavailability or profound side effects associated with peripheral activity.

Recent molecular biological studies have cloned five subtypes of muscarinic receptors, each with a unique amino acid sequence, tissue-specific expression, ligand binding profile and associated biochemical response. Each subtype is expressed within the central nervous system, although m1, m3 and m4 receptors predominate in the cerebral cortex and hippocampus. In peripheral tissues, the heart expresses m2 receptors while m3 receptors are found in exocrine glands. Pirenzepine, AF-DX 116 and p-F-hexahydrosiladifenidol are selective antagonists for $M_1$, $M_2$ and $M_3$ receptors respectively. These subtypes (m1, m3 and m5) couple selectively to the stimulation of phosphoinositide metabolism while m2 and m4 more efficiently inhibit adenylyl cyclase.

In addition to the recent studies showing the preferential localization of $M_1$ receptors in the cerebral cortex and hippocampus, recent findings also show that $M_1$ antagonists, such as pirenzepine, produce memory impairments in experimental animals.

Thus, it will be appreciated by those skilled in the art that what is needed in the art to reverse the cognitive and memory deficits associated with a loss of cholinergic neurons, as found in Alzheimer's disease, is a selective muscarinic agonist with high central nervous system activity. This agonist should bind selectively to $M_1$ muscarinic receptors, localized predominantly in the cerebral cortex and hippocampus. It should stimulate phosphoinositide metabolism in the hippocampus.

Even more broadly, however, there is a need in the art to provide muscarinic agonists which have activity at various muscarinic receptor subtypes in the central and peripheral nervous system.

OBJECTS OF THE INVENTION

It is an object of the present invention to satisfy the above need in the art with amidine derivative compounds hereinafter disclosed.

It is an object of the present invention to provide a compound having the formula (I) or (II) below or a pharmaceutically acceptable salt thereof:

where R is (trans) 3-methyl-2-penten-4-ynyl, (cis)3-methyl-2-penten-4-ynyl, 2-butynyl, 2-methylbutenyl, 3-methylpropynyl, phenylpropynyl, butynyl; or

where R' is butynyl.

It is an object of the present invention to provide a pharmaceutical preparation effective for stimulating a muscarinic receptor and also to provide a method for providing a therapeutic benefit to a mammal by administering to the mammal the certain amidine derivative muscarinic agonist compounds.

These and other objects will be apparent from the specification that follows and the appended claims.

SUMMARY OF THE INVENTION

The present invention provides a compound having the formula (I) or (II) below or a pharmaceutically acceptable salt thereof:

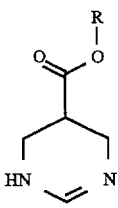

(I)

where R is (trans) 3-methyl-2-penten-4-ynyl, (cis)3-methyl-2-penten-4-ynyl, 2-buynyl, 2-methylbutenyl, 3-methylpropynyl, phenylpropynyl, butynyl;

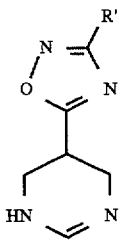

(II)

where R' is butynyl.

The invention also provides a pharmaceutical preparation effective for stimulating a muscarinic receptor, comprising the above described compounds, or a pharmaceutically acceptable salt thereof, together with a pharmaceutically acceptable solid or liquid carrier.

The present invention also provides a method of providing a therapeutic benefit to a mammal comprising administering to said mammal a drug in effective amounts to stimulate a muscarinic receptor so as to provide such benefit, the improvement wherein said drug is an above described compound or its pharmaceutical salt.

DETAILED DESCRIPTION OF THE INVENTION

In therapeutic uses as agents for treating cholinergic insufficiency, the compounds utilized in the pharmaceutical method of this invention are desirably administered to the patient in amounts effective to stimulate muscarinic receptors and thereby stimulate central and/or peripheral nervous systems. Since the compounds of this invention will stimulate central muscarinic acetylcholine receptors they are useful when administered in effective amounts, to treat not only presenile and senile dementia but also Huntington's chorea, tardive dykinesia, hyperkinesia, mania and Tourcite syndrome. In effective amounts, they are also useful as analgesics, for example, in treating painful conditions like rheumatism, arthritis and terminal illness and they are useful in the peripheral nervous system to treat glaucoma and atonic bladder conditions.

The specific dosages employed may vary depending upon the requirements of the patient, the severity of the condition being treated and the activity of the compound being employed. The determination, however, may vary depending upon the requirements of the patient, the severity of the condition being treated and the activity of the compound being employed. The determination, however of optimum dosages for any particular situation is well within the skill of the art.

In preparing pharmaceutical compositions of the compounds (or their pharmaceutically acceptable salts) of this invention, inert, solid or liquid pharmaceutically acceptable carriers will be employed. Sold form preparations include powders, tablets, dispersible granules, capsules, cachets, and suppositories.

A solid carrier can be one or more substances which may also act as diluents, flavoring agents, solubilizers, lubricants, suspending agents, binders, or table disintegrating agents; it can also be an encapsulating material.

In powders, the carrier is a finely divided solid which is in a mixture with the finely divided active components. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tables preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a long-melting wax, cocoa butter, and the like.

The term "preparation" is intended to comprehend within its scope a formulation of the active compound with encapsulating material as a carrier, thereby providing a capsule in which the active component (with or without other carriers) is surrounded by a carrier and is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol are mentioned as examples of liquid preparations suitable for parenteral administration.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, or other suspending agents known to the pharmaceutical formulation art.

Preferably, the pharmaceutical preparation is in unit dosage form. In such form, the preparation is divided into unit does containing appropriate quantities of the active component. The unit dosage form can be a package preparation, the package containing discrete quantities of the preparation, for example, packeted tablets, capsules, and powders in vials or ampoules. The unit dosage form can also be a capsule, cachet, or tablet itself.

In the aforementioned U.S. Pat. No. 5,175,166 in column 32, Table 1 shows test results of 15 compounds including some suitable muscarinic agonists that bind and act. In commenting upon the results, in column 33, two sentences in lines 3–7 state as follows:

Thus the unpredictable nature of this technology will be readily apparent. Changing a hydrogen atom (Ex.10) to a methyl group (Ex. 19) resulted in the production of an inactive and unacceptable composition.

Surprisingly, in the present invention, the disclosed amidine derivatives show unusual and excellent results as illustrated in Table 1.

solid (0.6 g, 58 %) of 5-(3-methylisoxazol-5-yl)-1,4,5,6-tetrahydropyrimidine as the trifluoroacetate salt: $^1$H NMR ($D_2O$): δ2.30 (3H, d, $CH_3$), 3.10 (1H, m), 3.50 (4H, d), 6.35 (1H, s, isoxazole-H), 7.8 (1H, s, amidine-H); MS m/z 165 ($M^+$ of free base). Anal. ($C_{10}H_{12}N_3O_3F_3$) C, H, N.

TABLE 1

Binding affinities and agonist activity in a series of amidine derivatives at muscarinic receptors in the rat central nervous system. Data represent the mean from one to three experiments, each performed in triplicate.

| Chemical Structure | Functionality | Ligand | $IC_{50}$ [$^3$H]-QNB | PI cortex (at 100 µM) |
|---|---|---|---|---|
| R = | (trans) 3-methyl-2-penten-4-ynyl, | CDD-0161-A | 4.1 ± 0.63 µM | 35 ± 5.6% |
| | (cis)3-methyl-2-penten-4-ynyl, | CDD-0162-A | 1.5 ± 0.42 µM | 50 ± 4.3% |
| | 2-butynyl, | CDD-0171-A | 15 ± 0.42 µM | 140 ± 4.1% |
| | 2-methylbutenyl, | CDD-0176-A | 38 ± 16 µM | 24 ± 12% |
| | 3-methylpropynyl, | CDD-0177-A | 45 ± 0.55 µM | 22 ± 3% |
| | phenylpropynuyl, | CDD-0189-A | 9.3 ± 1.5 µM | 23 ± 8.2% |
| | butynyl; | CDD-0195-A | 14 ± 2.8 µM | 100 ± 15% |
| R' = | butynyl | CDD-0194-J | 16 ± 6.9 µM | 130 ± 18% |

The following examples illustrate the preparation of the superior and unusual muscarinic agonist compounds.

EXAMPLE 1

5-(3-Methyl-1,2-isoxazol-5-yl)-1,4,5,6-tetrahydropyrimidine trifluoroacetate (18)

A solution of n-butyllithium in hexane (2.5M, 1.8 mL, 5.2 mmol) was added to a stirred solution of acetone oxime (0.2 g, 2.6 mmol, Aldrich) in dry THF (30 mL) under a nitrogen atmosphere at 0° C. (ice-salt bath) to give a grey suspension. Stirring continued below 0° C. for a period of 1 h. After stirring for 1 h, a solution of 1-(trityl)-(5-methyloxycarbonyl)-1,4,5,6-tetrahydropyrimidine (1 g, 2.6 mmol) in dry THF (20 mL) was added all at once to the mixture, and the solution was allowed to warm to 22° C. over 18 h. The mixture was poured into a stirred solution of concentrated sulfuric acid (2.4 mL) in THF (20 mL) and water (6 mL) and heated with stirring under reflux for 1 h. The cooled solution was made basic with aqueous potassium carbonate (2M, 100 mL). An additional 200 mL portion of water was added to facilitate the extraction process. The mixture was extracted (5×200 mL) with dichloromethane and the extracts were dried ($MgSO_4$). The residue obtained on removal of solvents in vacuo was chromatographed (silica, chloroform/methanol, 9:1) to give a residue of the tritylated product $R_f$ 0.40. The crude product was dissolved in TFA (3 mL) and the resulting yellow solution was warmed gently overnight for 24 h. Removal of excess solvents in vacuo gave a pale-brown residue. The residue was washed with hexane (6×75 mL), and the supernatant decanted to give a pale-brown semi-solid. Recrystallization of the residue from methanol and THF gave a brown, viscous semi-

EXAMPLE 2

(cis)-5-(3-Methyl-2-penten-4-ynyloxycarbonyl)-1,4,5,6-tetrahydropyrimidine HCl (25a)

A mixture of 1,4,5,6-tetrahydropyrimidine-5-carboxylic acid chloride (0.4 g) and (cis)-3-methyl-2-penten-4-yn-1-ol (15 mL, excess) was stirred at room temperature overnight. The reaction mixture was taken up in water 100 mL), stirred at room temperature for 2 h and filtered. The dark-brown residue obtained on removal of solvents in vacuo was recrystallized (ethanol/ether) to give a brown viscous oil (0.4 g, 67 %) of (cis)-5-(3-methyl-2-penten-4-ynyloxycarbonyl)-1,4,5,6-tetrahydropyrimidine as the hydrochloride salt. $^1$H NMR ($D_2O$): δ1.8 (m, 3H), 3.09 (m, 1H), 3.46 (s, 1H), 3.50 (d, 4H), 4.15 (d, 2H, $OCH_2$), 5.8 (t, 1H, =$CHCH_2O$), 7.90 (s, 1H, amidine-H). Anal. ($C_{11}H_{15}N_2O_2Cl$) C, H, N.

EXAMPLE 3

(trans)-5-(3-Methyl-2-penten-4-ynyloxycarbonyl)-1,4,5,6-tetrahydropyrimidine HCl (25b)

1,4,5,6-tetrahydropyrimidine-5-carboxylic acid hydrochloride (1 g, 6 mmol) was suspended in a solution of oxalyl chloride (1.5 mL, 17 mmol) in benzene (10 mL), heated with stirring under reflux for 2.5 h, and then evaporated to dryness in vacuo after cooling, to give an orange-yellow residue. The last traces of oxalyl chloride were removed by adding 10 mL of benzene to the residue, then the residue was evaporated to dryness in vacuo to give an orange residue of the crude acid chloride. A mixture of the acid chloride (0.4 g) and (trans)-3-methyl-2-penten-4-yn-1-ol (10 mL, excess)

was stirred at room temperature overnight. The reaction mixture was taken up in water (100 mL), stirred at room temperature for 2 h and filtered. The dark-brown residue obtained on removal of solvents in vacuo was recrystallized (ethanol/ether) to give yellow crystals (0.3 g, 64 %) of (trans)-5-(3-methyl-2-penten-4-ynyloxycarbonyl)-1,4,5,6-tetrahydropyrimidine as the hydrochloride salt: mp 144°–145° C.; $^1$H NMR (D$_2$O); δ 1.8 (m, 3H), 3.09 (m, 1H), 3.44 (s, 1H), 3.50 (d, 4H), 4.18 (d, 2H, OCH$_2$), 5.9 (t, 1H, =CHCH$_2$O), 7.80 (s, 1H, amidine-H). Anal. (C$_{11}$H$_{15}$N$_2$O$_2$CL) C, H, N.

EXAMPLE 4

5-(2-Butynyloxycarbonyl)-1,4,5,6-tetrahydropyrimidine HCl (25c)

1,4,5,6-tetrahydropyrimidine-5-carboxylic acid hydrochloride (1 g, 6 mmol) was suspended in a solution of oxalyl chloride (1.5 mL, 17 mmol) in benzene (10 mL), heated with stirring under reflux for 2.5 h, and then evaporated to dryness in vacuo after cooling, to give an orange-yellow residue. A mixture of the acid chloride (04 g) and 2-butyn-1-ol (20 mL, excess) was stirred at room temperature overnight. After stirring overnight, the solvents were removed in vacuo to give a brownish residue. The residue was taken up in water (100 mL), stirred at room temperature for 2 h and filtered. The brown residue obtained on removal of the solvents in vacuo was recrystallized (ethanol/ether) to give a brown viscous oil (0.3 g, 61%) of 5-(2-butynyloxycarbonyl)-1,4,5,6-tetrahydropyrimidine as the hydrochloride salt. $^1$H NMR (D$_2$O): δ 1.5 (t, 3H, CH$_3$), 3.1 (m, 1H), 3.5 (d, 4H), 3.9 (q, 2H, OCH$_2$), 7.9 (s, 1H, amidine-H). Anal. (C$_9$H$_{13}$N$_2$O$_2$Cl) C, H, N.

EXAMPLE 5

5-(2-Methylbutenyloxycarbonyl)-1,4,5,6-tetrahydropyrimidine HCl (25d)

A mixture of 1,4,5,6-tetrahydropyrimidine-5-carboxylic acid chloride (0.5 g, 2.7 mmol) and 3-methyl-2-buten-1-ol (20 mL, excess) was stirred at room temperature overnight. After stirring overnight the solvents were removed in vacuo to give a reddish residue. The residue was taken up in water (100 mL), stirred at room temperature for 2 h and filtered. The residue obtained on removal of solvents in vacuo was recrystallized (ethanol/ether) to give a brown viscous oil (0.4 g, 59 %) of 5-(2-methylbutenyloxyearbonyl)-1,4,5,6-tetrahydropyrimidine as the hydrochloride salt. $^1$H NMR (D$_2$O): δ 0.9 (s, 6H), 1.5 (m, 1H, CH—), 3.1 (m, 1H), 3.5 (d, 4H), 3.9 (m, 2H, OCH$_2$), 7.8 (s, 1H, amidine-H). Anal. (C$_{10}$H$_{17}$N$_2$O$_2$CL), C, H, N.

EXAMPLE 6

5-(3-Methylpropynyloxycarbonyl)-1,4,5,6-tetrahydropyrimidine HCl (25e)

A mixture of 1,4,5,6-tetrahydropyrimidine-5-carboxylic acid chloride (0.5 g, 2.7 mmol and 3-methylbutyn-2-ol (15 mL, excess) was stirred at room temperature overnight. After stirring overnight the solvents were removed in vacuo to give a residue. The residue was taken up in water (50 mL), stirred at room temperature for 2 h and filtered. The residue obtained on removal of solvents in vacuo was recrystallized (ethanol/ether) to give a red viscous oil (0.2 g, 54%) of 50(3-methylpropynyloxycarbonyl)-1,4,5,6-tetrahydropyrimidine as the hydrochloride salt. $^1$H NMR (D$_2$O): δ 1.5 (s, 3H, CH$_3$), 2.3 (d, 1H, acetylenic-H), 3.09 (m, 1H), 3.5 (d, 4H), 3.8 (d, 1H, OCH—), 7.9 (s, 1H, amidine-H). Anal. (C$_9$H$_{13}$N$_2$O$_2$Cl) C, H, N.

EXAMPLE 7

5- Phenylpropynyloxycarbonyl)-1,4,5,6-tetrahydropyrimidine HCl (25g)

A mixture of 1,4,5,6-tetrahydropyrimidine-5-carboxylic acid chloride (1 g, 6 mmol) and 3-phenyl-2-propyn-1-ol (10 mL, excess, Lancaster) was stirred at room temperature overnight. After stirring overnight, attempts to remove solvents both under reduced pressure and high vacuum were not successful. Since the desired product is soluble in water, the reaction mixture was taken up in water (100 mL), then extracted (2×150 mL) with diethyl ether. The aqueous layer was washed with another 100 mL portion of ether, filtered and evaporated to dryness in vacuo to give an orange-yellow, viscous, oily residue of the crude product. The first recrystallization from ethanol and THF gave beige crystals (50 mg), mp 158°–159° C. $^1$H NMR taken in deuteromethanol indicated this compound was an impurity. The filtrate from the first recrystallization was evaporated to dryness in vacuo to give an orange-yellow viscous oily residue. The residue was dissolved with heat in anhydrous methanol (20 mL) and concentrated to half the volume. Diethyl ether was added and after shaking thoroughly for 10 minutes, the ether layer was decanted. The pale-yellow residue remaining inside the flask was air-dried, dry THF was added and crystals began to form. After leaving overnight inside the refrigerator, crystals were collected by filtration, dried in a vacuum oven at 50° C. for 3 h to give white crystals (0.4 g, 62 %) of 5-(phenylpropynyloxycarbonyl)-1,4,5,6-tetrahydropyrimidine as the hydrochloride salt: mp 117°–118° C.; $^1$H NMR (CD$_3$OD): δ 3.2 (m, 1H), 3.6 (d, 4H), 4.9 (s, 2H, OCH$_2$), 7.3–7.5 (multiplet, aromatic-5H), 7.9 (s, 1H). Anal. (C$_{14}$H$_{15}$N$_2$O$_2$Cl) C, H, N.

EXAMPLE 9

5-(3-(Butyn-1-yl)-1,2,4-oxadiazol-5-yl)-1,4,5,6-tetrahydropyrimidine Trifluoroacetate (26)

1- (Triphenymethyl)-5-(3 (butyn-1-yl)-1,2,4-oxadiazol-5-yl) -1,4,5,6-tetrahydropyrimidine was dissolved in trifluoroacetate (3 mL) with stirring, and the yellow solution warmed gently overnight for 24 h. The resulting dark solution was evaporated in vacuo, and the residue was triturated with hexane (6×10 mL). The hexane layers were decanted and the residue was recrystallized (ethanol/ether) to yield 120.mg (40 %) of viscous product. $^1$H NMR (D$_2$O): δ 2.25 (t, 1H, acetylenic-H), 2.5 (q, 2H), 2.6 (t, 2H), 3.10 (m, 1H), 3.50 (d, 4H), 7.8 (s, 1H, amidine-H); MS m/z 204 (M$^+$of free base). Anal. (C$_{12}$H$_{13}$F$_3$N$_4$O$_3$) C, H, N.

What is claimed is:
1. A compound having the formula (II) below or a pharmaceutically acceptable salt thereof:

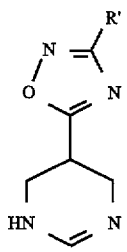 (II)

where R' is butynyl.

2. A pharmaceutical composition effective for stimulating a muscarinic receptor, comprising a compound of claim 1, or a pharmaceutically acceptable salt thereof, together with a pharmaceutically acceptable solid or liquid carrier.

3. In a method of providing a therapeutic benefit to a mammal comprising administering to said mammal a drug in an effective amount to stimulate a muscarinic receptor so as to provide such benefit, the improvement where in said drug is a compound of claim 1 or a pharmaceutically acceptable salt thereof.

* * * * *